(12) United States Patent
Roma et al.

(10) Patent No.: US 11,396,674 B2
(45) Date of Patent: Jul. 26, 2022

(54) MULTIPLEX NUCLEIC ACID AMPLIFICATION AND LIBRARY PREPARATION

(71) Applicants: Gianluca Roma, Belmont, CA (US); Katie Leigh Zobeck, Sunnyvale, CA (US)

(72) Inventors: Gianluca Roma, Belmont, CA (US); Katie Leigh Zobeck, Sunnyvale, CA (US)

( * ) Notice: Subject to any disclaimer, the term of this patent is extended or adjusted under 35 U.S.C. 154(b) by 29 days.

(21) Appl. No.: 16/779,597

(22) Filed: Feb. 1, 2020

(65) Prior Publication Data

US 2020/0270672 A1 Aug. 27, 2020

Related U.S. Application Data

(60) Provisional application No. 62/809,542, filed on Feb. 22, 2019.

(51) Int. Cl.
| | | |
|---|---|---|
| *C12Q 1/686* | (2018.01) | |
| *C12N 9/12* | (2006.01) | |
| *C12N 9/00* | (2006.01) | |

(52) U.S. Cl.
CPC ........... *C12Q 1/686* (2013.01); *C12N 9/1252* (2013.01); *C12N 9/93* (2013.01); *C12Q 2537/143* (2013.01); *C12Q 2600/156* (2013.01)

(58) Field of Classification Search
CPC ............. C12Q 1/686; C12Q 2537/143; C12Q 2600/156; C12Q 1/6848; C12N 9/1252; C12N 9/93
See application file for complete search history.

(56) References Cited

U.S. PATENT DOCUMENTS

| | | |
|---|---|---|
| 5,580,730 A | 12/1996 | Okamoto |
| 2011/0244452 A1* | 10/2011 | Cookson .............. C12Q 1/6848 435/6.11 |
| 2013/0045894 A1 | 2/2013 | Frey et al. |
| 2014/0051068 A1 | 2/2014 | Cherf et al. |
| 2016/0230222 A1* | 8/2016 | Liu ........................ C12Q 1/686 |
| 2018/0037946 A1 | 2/2018 | Seebeck et al. |

OTHER PUBLICATIONS

Huang et al. "Hemi-nested touchdown PCR combined with primer-template mismatch PCR for rapid isolation and sequencing of low molecular weight gluterin subunit gene family fan a hexaploid wheat BAC library," BMC Genetics. May 4, 2007 (May 4, 2007), vol. 8, Iss. 18, pp. 1-9.
PCT International Search Report for International application No. PCT/US2020/016655 dated Apr. 30, 2020.
Pisapia at al. Consistency and reproducability of next-generation sequencing in cytopathology: A second worldwide ring trial study on improved cytological molecular reference specimens. Cancer Cytopathology. Apr. 25, 2019 (Apr. 25, 2019), vol. 127, Iss. 5, pp. 265-296.

* cited by examiner

*Primary Examiner* — Cynthia B Wilder
(74) *Attorney, Agent, or Firm* — Jeffery D. Frazier

(57) ABSTRACT

Processes and kits for preparing a plurality of multiplex amplification products for targeted next generation-sequencing providing reduced background noise.

8 Claims, 7 Drawing Sheets

MULTIPLEX NUCLEIC ACID AMPLIFICATION AND LIBRARY PREPARATION

CROSS-REFERENCE TO RELATED APPLICATIONS

This patent application claims priority to U.S. Provisional Patent Application No. 62/809,542 filed Feb. 22, 2019, which application is incorporated herein by reference in its entirety.

FIELD

The present teachings relate to methods, compositions, and kits for performing DNA library preparation for use with massively parallel DNA sequencers using high fidelity multiplex nucleic acid amplification for target enrichment. In particular, the present teachings relate to methods, compositions, and kits for high multiplex amplification and subsequent reduction of interfering non-specific amplification by-products during sequencing.

BACKGROUND

Multiplex PCR is a widespread molecular biology technique for the amplification of multiple targets in a single PCR experiment. Multiplex PCR is often employed in amplification-based massively-parallel next-generation sequencing DNA library preparation, as it can allow for increased targeted coverage in a single tube reaction.

Although its utility is unquestioned, multiplex PCR can be particularly difficult to optimize. Because a unique primer pair is included for each additional target, reactions become more prone to off-target amplification, such as mispriming and primer dimerization, than traditional single-plex pair PCR setups. These non-specific amplification by-products can hinder the sensitivity and specificity during the downstream DNA sequencing reaction thereby reducing the signal-to-noise ratio obtained during final sequence analysis.

There is an ongoing need to improve the amplification fidelity of multiple targeted regions of a genome in multiplex PCR (or for any nucleic acid amplification) reaction for target enrichment while reducing by-products formation such as primer-dimers and other off-target products such as, single-stranded overhangs, DNA mismatches, or non-perfectly-matched DNAs, which may carry over into downstream sequencing reaction resulting in increased background noise and/or reduced signal.

SUMMARY

An exemplary and non-limiting summary of various embodiments is set forth next.

Various aspects of the present teachings relate to a novel approach to remove PCR amplification by-products that employs a protecting group (also referred to as a nuclease resistant group) in the PCR primer composition. When the modified PCR primer containing the protecting group is combined and reacted with specific exonucleases and kinases simultaneously, partial digest of the primer and non-specific by-products of amplifications, including unused PCR primers are substantially reduced or eliminated.

Further aspects of the present teachings relate to the use of multiplex PCR amplification to enrich multiple targets of interest while reducing post-amplification by-products via controlled primer digestion for use during the preparation of massively-parallel next-generation DNA sequencing library construction.

Various aspects of the present teachings relate to a protocol for DNA library preparation for targeted next generation-sequencing providing low background noise. According to various embodiments, a multiplexed amplification reaction is provided comprising at least two primer pairs employing a plurality of primers having the structure:

5' end-primer binding region-protecting group-3', wherein the 3' protecting group comprises no greater than 4 phosphorothioates.

According to various embodiments, the 3' protecting group is resistant from exonuclease hydrolysis.

In various embodiments, the protecting group is comprised of a phosphorothioate bond at the 3' terminal.

According to various embodiments, the amplification method comprises multiplexed PCR.

In various embodiments, a kinase is used to provide a 5' terminal phosphate group.

In accordance with various embodiments, amplification is performed using any suitable DNA polymerase capable of extending a primer with nucleotides comprising a 3' protecting group.

According to various embodiments, the 5' end of a sequence is digested using one or more exonucleases that are double-strand DNA specific and have 5'>3' directionality and terminate when encountering the protecting group on the 3' end of the primer.

In various embodiments, the 3' end of a sequence is digested using one or more exonucleases and/or proofreading polymerases that can attack 3' overhangs and are double-strand DNA specific with a 3'>5' directionality that terminates when the enzyme encounters the opposite DNA strand.

According to various embodiments, a 5' phosphate group is formed via a T4 polynucleotide kinase for preparation of the primers before amplification.

In various embodiments, a 5' phosphate group is added to the 5' end of the PCR primer via a T4 polynucleotide kinase during multiplex PCR amplification step.

According to various embodiments, a 5' phosphate group is added to the PCR amplification product 5' ends using a T4 polynucleotide kinase during the primer digestion step.

In various embodiments, a 5' phosphate group is added to the PCR digested product 5' ends using a T4 polynucleotide kinase during the adaptors ligation step.

According to various embodiments, lambda exonuclease is added to the digestion mixture.

In various embodiments, T4 DNA polymerase is added to the digestion mixture.

According to various embodiments, one or more dNTPs, such as dATP, is in excess in the digestion mixture.

Further aspects of the present teachings relate to a protocol for library preparation for targeted next gen-sequencing DNA sequencing providing low background noise and high accuracy. In accordance with various embodiments, a multiplexed amplification reaction comprises at least two primer pairs employing a plurality of primers having the structure:

5' end-primer binding region-protecting group-3', wherein the 3' protecting group comprises at least one phosphorothioate group.

In some embodiments, the structure comprises:

5'-single mismatch base-primer binding region-protecting group-3'.

In various embodiments, the 3' end comprises no more than four protecting groups. For example, the 3' end can comprise one, two, three, or four protecting groups.

Still further aspects of the present teachings relate to a process for preparing a plurality of multiplex amplified nucleic acid products for targeted next generation-sequencing providing reduced background noise. In various embodiments, such process comprises: (a) contacting one or more nucleic acids with at least two pairs of non-5'phosphorylated amplification primers and a DNA polymerase under amplification conditions to form a plurality of amplification products, each amplification primer comprising at least one and no more than four protecting groups in its 3' region; and wherein the protecting groups are phosphorothioate bonds; (b) contacting the plurality of amplification products with a 5' to 3' exonuclease and either a 3' to 5' single strand-specific exonuclease or a proofreading polymerase to form a plurality of digested amplification products; wherein the plurality of digested amplification products has a reduced level of non-specific amplification artifacts as compared to a standard nucleic acid amplification reaction performed with primers devoid of protecting groups.

According to various embodiments, step (b) of the process further comprises contacting the plurality of amplification products with a plurality of dNTPs selected from the group consisting of dATP, dGTP, dCTP, and dTTP; wherein one of the dNTPs is present at a concentration that is higher compared to the concentration of the other dNTPs.

In various embodiments, the process further comprises contacting the plurality of amplification products, of step (b), with a 5' phosphorylating kinase. In various embodiments, the 5' phosphorylating kinase comprises T4 polynucleotide kinase (T4 PNK).

In various embodiments, the 3' to 5' exonuclease comprises T4 DNA polymerase.

According to various embodiments, the 5' to 3' single strand-specific exonuclease comprises lambda exonuclease.

According to various embodiments, the DNA polymerase lacks a proofreading activity. In other embodiments, the DNA polymerase comprises a proofreading activity. In some embodiments, the DNA polymerase comprising a proofreading activity comprises Pfu DNA polymerase.

According to various embodiments, step (b) is carried out at a reaction temperature of 40° C. or less. In other embodiments, step (b) is carried out at a reaction temperature of 20° C. or less. In some embodiments, step (b) is carried out at a reaction temperature of 10° C. or less.

In various embodiments, the amplification primers further comprise at least one terminal 5' base mismatch. For example, in various embodiments, the primers can comprise from one to fifteen terminal 5' base mismatches.

According to various embodiments, the excess dNTP is present at a concentration of at least 20 μM. According to some embodiments, the excess dNTP is present at a concentration of at least 100 ||M.

In various embodiments, the process further comprises ligating one or more adaptors to the plurality of digested amplification products to form a plurality of adaptor-ligated amplification products.

Additional aspects of the present teachings relate to a kit for preparing a plurality of multiplex amplification products for targeted next generation-sequencing providing reduced background noise. According to various embodiments, such a kit can comprise: (a) two or more pairs of non-5'phosphorylated amplification primers, each amplification primer comprising at least one and no more than four protecting groups in its 3' region; and wherein the protecting groups are phosphorothioate bonds; (b) a DNA polymerase; (c) a 5' to 3' exonuclease; (d) either a 3' to 5' single strand-specific exonuclease or a proofreading polymerase; and, (e) dNTP.

According to various embodiments, the kit can further comprise a plurality of dNTPs. For example, the kit can comprise dATP, dGTP, dCTP, and dTTP.

In various embodiments, the kit further comprises a 5' phosphorylating kinase. According to various embodiments, the 5' phosphorylating kinase comprises T4 polynucleotide kinase (T4 PNK).

In various embodiments, the kit further comprises one or more adaptors and a DNA ligase.

According to various embodiments, the 3' to 5' exonuclease comprises T4 DNA polymerase.

In various embodiments, the 5' to 3' single strand-specific exonuclease comprises lambda exonuclease.

In various embodiments, the DNA polymerase lacks a proofreading activity. In other embodiments, the DNA polymerase comprises a proofreading activity. In some embodiments, the DNA polymerase comprising a proofreading activity comprises Pfu DNA polymerase.

In various embodiments, the amplification primers further comprise a terminal 5' base mismatch. For example, in various embodiments, the primers can comprise from one to fifteen terminal 5' base mismatches, or more.

According to various embodiments, a kit according to the present teachings can further comprise instructions for carrying out the processes described herein.

Other aspects and iterations of the present teachings are further described below.

BRIEF DESCRIPTION OF THE DRAWINGS

Various embodiments of the disclosure will be discussed with reference to the following exemplary and non-limiting drawings, where.

DESCRIPTION

Figure 1:
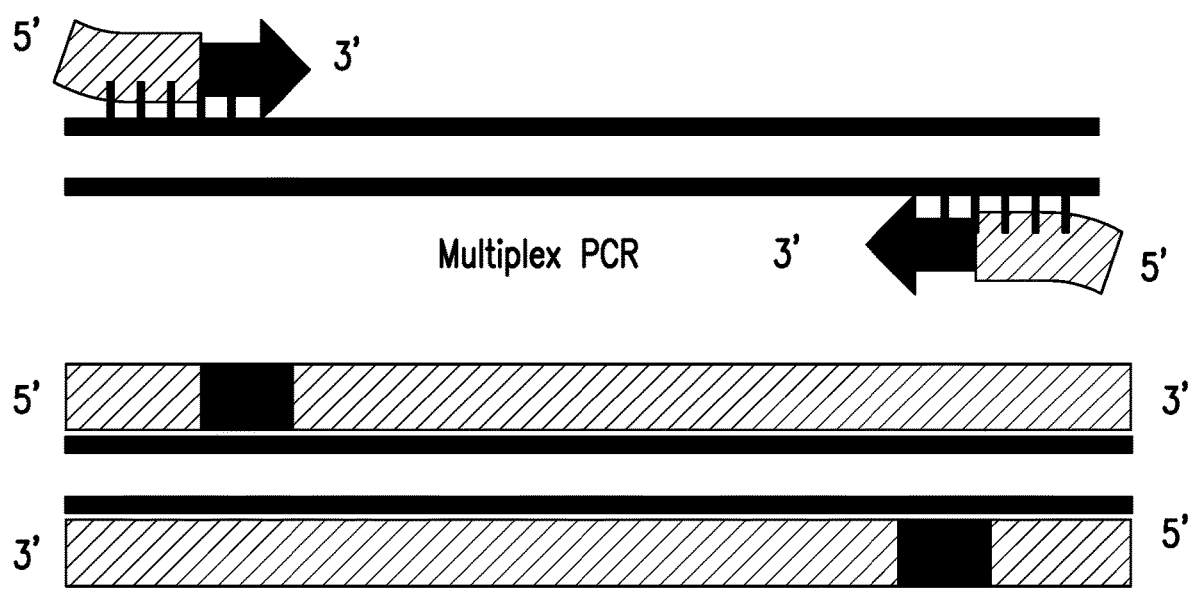
FIG. 1 schematically depicts the design of PCR primers using plural 3' phosphorothioate bonds and a terminal 5' base mismatch with target template.

Reference will now be made to various embodiments. While the present teachings will be described in conjunction with various embodiments, it will be understood that they are not intended to limit the present teachings to those embodiments. On the contrary, the present teachings are intended to cover various alternatives, modifications, and equivalents, as will be appreciated by those of skill in the art.

Among other things, various aspects of the present teachings relate to methods to improve the amplification fidelity of multiple targeted regions of a genome in a multiplex PCR (or any amplification) reaction while reducing by-products such as primer-dimers or other off-target products that may reduce the quality of the data that is generated and interfere with downstream analysis, such as for next-generation massively parallel DNA sequencing.

In one aspect, according to various embodiments, the present teachings relate to specific primer design, and in another aspect, according to various embodiments, the present teachings relate to an overall optimization of workflow that increases the efficiency of next-generation sequencing by targeting only user-defined regions of interest and substantially reducing or eliminating contaminating genomic DNA, and other interfering by-products of targeted amplification or unused reactants.

Polymerase chain reaction (PCR) is a common DNA amplification method used, among other ways, to enrich specific targeted regions in a genome before downstream targeted massively parallel next-generation DNA sequencing. Typically, a thermostable Taq polymerase is used in combination with buffers to amplify a sequence region between two flanking primers (forward and reverse oligomers). After targeted PCR amplification, the amplicons are ligated to short oligonucleotides that contain a known DNA sequence called a DNA adaptor via, typically, a T4 DNA ligase reaction. Upon DNA next-generation sequencing (NGS), the adaptor sequence is recognized by special software algorithms, which permit sequence alignment to a human reference genome (e.g., hg 19) and final variant calls are determined. (See, e.g., Voelkerding KV1, Dames S A, Durtschi J D. (2009) Next-generation sequencing: from basic research to diagnostics. Clin Chem. 2009 April; 55(4): 641-58; incorporated herein by reference.)

In clinical diagnostic applications, high-fidelity PCR is preferred since it enables the most accurate detection of a patient's DNA and thus allows the most accurate diagnosis. In various embodiments of the present teachings, Pfu DNA polymerase, a thermostable enzyme isolated from *Pyrococcus furiosus*, is used to provide high-fidelity PCR during the initial targeted amplification step (See, Fiala, G., & Stetter, K. O. (1986). *Pyrococcus furiosus* sp. nov. represents a novel genus of marine heterotrophic archaebacteria growing optimally at 100° C. *Archives of Microbiology*, 145, 56-61; incorporated herein by reference.)

Pfu DNA polymerase, in addition to having a 5' to 3' DNA polymerase activity, also possesses 3' to 5' exonuclease (proofreading) activity. It has been reported that the Pfu DNA Polymerase exhibits the lowest error rate of any thermostable DNA polymerase studied. Consequently, according to various embodiments, Pfu DNA Polymerase can be useful for polymerization reactions requiring high-fidelity synthesis. (See, Flaman J. M., Frebourg T., Moreau V., Charbonnier F., Martin C., Ishioka C., Friend S. H., Iggo R., Nucleic Acids Res., 1994, vol. 22 (pg. 3259-3260); Andre, P. et al. (1997) Fidelity and mutational spectrum of Pfu DNA polymerase on a human mitochondrial DNA sequence. Genome Res. 7, 843-52; Cline, J., Braman, J. C. and Hogrefe, H. H. (1996) PCR fidelity of Pfu DNA polymerase and other thermostable DNA polymerases. Nucl. Acid Res. 24, 3546-51; and, Lundberg, K. S. et al. (1991) High-fidelity amplification using a thermostable DNA polymerase isolated from *Pyrococcus furiosus*. Gene 108, 1-6; each of which is incorporated herein by reference.)

The accuracy (i.e., fidelity) of a polymerase is measured as the average number of nucleotides the polymerase incorporates before making an error. The error rate is the reciprocal value of accuracy and is expressed as the mutation rate per duplicated base pair. The accuracy of the Pfu DNA Polymerase has been reported to be $7.7 \times 10^5$ to $1 \times 10^6$. The same PCR-based assay has been used to demonstrate that the accuracy of Pfu DNA polymerase is approximately 2-fold higher than Vent® DNA polymerase (New England Biolabs, Inc.), and approximately 6-fold higher than Taq DNA Polymerase. (See, Andre, P. et al. (1997) Fidelity and mutational spectrum of Pfu DNA polymerase on a human mitochondrial DNA sequence. Genome Res. 7, 843-52; and, Cline, J., Braman, J. C. and Hogrefe, H. H. (1996) PCR fidelity of Pfu DNA polymerase and other thermostable DNA polymerases. Nucl. Acid Res. 24, 3546-51; each of which is incorporated herein by reference.)

To achieve high fidelity PCR, according to various embodiments, it can be desirable that the pH of the 10× Tris-based buffer in the amplification reaction be greater than 8.6 (at 25° C.). When Pfu DNA polymerase is used at a lower pH than optimal (e.g., pH 8.0), the fidelity of Pfu DNA Polymerase is generally no better than the fidelity of Taq DNA Polymerase. Therefore, it is typically desirable that the pH of the buffer be greater than or equal to pH 8.6 when practicing various embodiments of the present teachings.

If Pfu DNA polymerase were to be used with unmodified synthesized DNA primers, it would be advisable to take special precautions to prevent pre-mature primer digestion. Often, Pfu DNA polymerase is added last in the amplification reaction mixture, particularly following the addition of dNTPs, as the proofreading activity of the polymerase degrades the amplification primers resulting in non-specific amplification and reduced product yield.

To overcome primer degradation by Pfu DNA polymerase, longer primers with maximized GC-content are often used. The last fifteen (15) 5' bases are often protected from degradation, and as such, a good primer length is around 20-35 bases. However, longer primers significantly increase the cost to manufacture compared to shorter primers (e.g. 15-30 bases). Longer primers are also more likely to contain impurities (n-1) during manufacturing due to inherent inefficiency in preparation that may result in lower product yields. A longer primer may also be limited by the primer's designs in some genome regions.

In the present teachings, primers are designed to be protected from the 3' to 5' exonuclease (proofreading) activity of Pfu polymerase by introducing one or more protecting groups such as bridged internucleotide 5'-phosphorothioate bond(s) in up to four (i.e., in 1, 2, 3, or 4) consecutive bases at their 3' termini. (See, Skerra, A. (1992) Phosphorothioate primers improve the amplification of DNA sequences by DNA polymerases with proofreading activity. (Nucleic Acids Res. July 25; 20(14): 3551-3554; incorporated herein by reference.)

Phosphorothioate modified PCR primers have a significantly lower cost to synthesize compared to other modified PCR primers that are based on uridine. Phosphorothioate modified primers typically increase oligomer cost by only 20% more versus unmodified primers. Nevertheless, the increased fidelity of phosphorothioate primers in multiplex PCR is valuable. Furthermore, one can understand that in a multiplex PCR amplification enrichment there may be in the upward of 10,000 forward and 10,000 reverse primers in a single primer pool. Any reduction in costs of the primer manufacturing is appreciated.

In the present teachings, the use of 3' phosphorothioate modified primers combined with non-proofreading polymerases (e.g. Taq Polymerase) may be also able to reduce misincorporation on average 1.4-fold across all substrates. (See, Single Base Extension with Proofreading Polymerases and Phosphorothioate Primers: Improved Fidelity in Single-substrate Assays: Nucleic Acids Research, 2003, Vol. 31, No. 3 e7, which is incorporated herein by reference in its entirety.)

In various embodiments of the present teachings, the phosphorothioate modified PCR primers serve as a mechanism to reduce PCR by-products due to minimized off-target amplification due to the lower melting temperature of these primers.

According to various embodiments, a partial primer digestion step is comprised of a mixture of exonucleases that target double-stranded DNA in a 5'>3' direction and/or exonucleases that target single-stranded DNA with a 3'>5' direction. (See, e.g., U.S. Patent Publication No. US 2018/0037946; incorporated herein by reference.) In addition, according to the present teachings, a 5' phosphorylating kinase is added to the foregoing exonuclease mixture. The combination of exonuclease and kinase partially digest the primer's unprotected bases and then terminates at the protecting group near the junction where the amplicon's insert region (i.e. region of interest) begins.

In various embodiments of the present teachings, T4 polynucleotide kinase (T4 PNK) is used to phosphorylate the terminal 5' end of the unphosphorylated PCR primers, thus allowing 5'>3' digestion of the nucleotides by double strand DNA specific Lambda exonuclease.

The result of controlled digestion of the primers not only removes primer-dimers but also removes unused single-stranded PCR primers in a single step.

PCR Primer Design:

According to various embodiments, the primer design includes a method by which a portion of the primer is partially digested after PCR amplification, leaving primarily the target region of interest which is subsequently analyzed via DNA sequencing.

Primers are designed to keep GC % content between 30-60% for all primers and oligo length between 17-35 bp long, using the Primer3 software and manual checking. Other examples of software that can be used to generate the multiplex primers are DNAsoftware's Visual OMP, Multi-PLX, ABI's Primer Express and MP Primer.

PCR primers can be designed to accommodate low quality formalin-fixed paraffin-embedded tissue (FFPE) DNA samples. These primer designs typically target between 75-250 bases for the amplicon size. However, amplicon size range can be significantly longer when targeting high-quality genomic DNA.

Primers can be designed to overlap between the upstream 5' end of one PCR primer and the 3' end of a downstream PCR primer by one or more bases without significant performance loss. In one embodiment, primers are designed to overlap by up to 7 base pairs of the 3' end of a forward primer and the 5' end of the adjacent forward primer within the same primer pool.

In other embodiments, multiplex PCR primers are designed to have the terminal 5' base mismatch the target DNA template by one or more bases. Surprisingly, a terminal 5' base mismatch to the target template permits a more consistent Lambda exonuclease attack especially when combined with a kinase such as T4 PNK.

Protected Primers:

A primer pair is synthesized to contain a protecting group and is designed in pairs that are specific to each region of interest (ROI), e.g., within a genome, transcriptome or methylome. The primer sequences contain one or more bases that are specific to the binding region (by complementary hybridization) to sequences flanking the target region.

In some embodiments, the 5' terminal end of the PCR primer is phosphorylated during oligo synthesis. In other embodiments a 5' unphosphorylated PCR primer is used. The primary function of the 5' phosphate group is to enhance the recognition by Lambda exonuclease, thereby allowing the exonuclease digestion reaction to proceed.

In the absence of a 5' phosphorylated PCR primer, the Lambda exonuclease 5'>3' digestion is negligible. PCR primers are generally synthesized without a 5' phosphate group. The addition of a 5' phosphate group during oligomer synthesis for a highly multiplex PCR panel would incur significantly higher costs compared to unphosphorylated PCR primers.

On the 3' end of the primer, typically between the $2^{nd}$ and $5^{th}$ base, there are no more than four consecutive phosphorothioate bonds. The phosphorothioate bond between nucleotides of the PCR primer render the nucleotides resistant to exonuclease digestion and also protect the primer from digestion from the exonuclease 3'>5'proofreading activity of the high fidelity Pfu DNA polymerase.

Generally, according to various embodiments, a PCR primer in accordance with the present teachings can comprise the following structure:

5' end-primer binding region-3' protecting group(s).

More particularly, for example, such a primer can include 1, 2, 3, or 4 consecutive 3' phosphorothioate bonds. In some embodiments, the primer includes no more than four 3' phosphorothioate bonds. For example, in various embodiments, the primer can include no more than one, no more than two, no more than three, or no more than four phosphorothioate bonds.

In other embodiments, a PCR primer in accordance with the present teachings can comprise the following structure:

5' mismatch base-primer binding region-3' protecting group(s).

More particularly, for example, such a primer can include 1, 2, 3, or 4 consecutive 3' phosphorothioate bonds and a terminal 5' base mismatch.

FIG. 1 schematically depicts the design of PCR primers using plural 3' phosphorothioate bonds and, in addition, a terminal 5' base mismatch with target template.

Several variations are contemplated, from the design of the primer to the adaption of the workflow. The specific chemical modifications of the primer may differ, but the important aspects of the modifications will remain.

The phosphorothioate bonds slightly increase the binding affinity of an oligo to the target template by reducing the Tm. The addition of C-5 propyne pyrimidines into the phosphorothioate oligos or 2'O methyl or Locked Nucleic Acid (LNA) bases can increase the base binding affinity even further. OXP modification at the terminal 3' end can enhance the sensitivity and specificity of the target amplification.

In some embodiments, the 5' terminal base of the PCR primers is intentionally mismatched with target template. Surprisingly, a terminal 5' base mismatch permits synergistic attack from Lambda exonuclease especially when paired with a kinase such as T4 PNK in a reaction that contains excess dATP.

Any suitable protecting group can be employed to block exonuclease digestion. Examples of protecting groups include: Phosphorothioate (S-oligo) R or S diastereomers or a mix of both diastereomers modified bases; Linkers C3, C6, C12, 5' aminothymidine or, 5-o-methylthymidine modified bases, 5' (C2-EDTA)-2' Deoxyuridine modified base, fluorinated or brominated modified bases, isobases modified bases (e.g. isoC and IsoG) modified bases, LNA bases. (See, e.g., Modified Oligonucleotides Synthesis and strategy for users. (Arum. Rev. Biochem. 1998. 67:99-134; incorporated herein by reference.)

Multiplex PCR Amplification:

Although multiplex PCR is generally preferred for nucleic acid amplification, in accordance with various embodiments, other nucleic acid amplification methods such as PCR, TMA, HDA, RPA, rolling circle, etc. can be used.

In various embodiments, a high-fidelity polymerase such as Pfu or VENT® polymerase is employed. Pfu, for example, allows for enhanced accuracy, especially when combined with phosphorothioate modified primers.

Below is an exemplary list of polymerases useful for nucleic acid amplification, in accordance with various embodiments:

Pfu (Agilent), Pfu (exo-), Taq, Vent, Taq Stoffel, Vent (exo-), Deep Vent® (exo-), Tth, Tfl, Hot Tub, Ultma, Vent, PWO, Tli, iProof (Bio-Rad), Pfu Turbo Cx (Agilent), Klenow Large Fragment, KOD, KOD (Plus), Q5 DNA Polymerase (NEB), reverse transcriptase.

(See, e.g., Protocols in Molecular Biology 3.5.1-3.5.19, October 2008; incorporated herein by reference.)

According to various embodiments, the following multiplex PCR thermal cycling parameters are used:

| Stage | Step | Temperature | Time |
| --- | --- | --- | --- |
| DNA polymerase activation | Denature | 95° C. | 10 min. |
| Cycle | Denature | 99° C. | 15 sec. |
| Cycle (2-35) | Extension | 60° C. | 4 min. |
| Hold | Stop | 10° C. | Infinity |

Partial Primer Digestion:

After target amplification, a mixture of exonucleases and kinases are added to the amplified products to partially digest the amplicons, non-specific by-products, and unused PCR primers.

In some embodiments, 5' unphosphorylated PCR primers are used during amplification, and a T4 polynucleotide kinase (T4 PNK) is included in the exonuclease enzyme digestion mixture to functionalize the amplicon with a terminal 5'phosphate. The reaction can proceed inconsistently without a terminal 5' phosphate.

Sequentially, lambda exonuclease, a double-stranded specific DNA exonuclease, catalyzes the removal of nucleotides in a 5'>3' releasing monomer base (dNMP), one at a time, until the phosphorothioate is encountered terminating the exonuclease hydrolysis.

The terminal 5' phosphate amplicons, functionalized by the T4 PNK, enables the digestion of unamplified and unused single-stranded PCR primers further by lambda exonuclease.

In various embodiments, supplementing the digestion enzyme mixture with T4 PNK in the presence of 1 mM dATP further benefits T4 DNA polymerase by shifting the reaction towards exonuclease rather than polymerization.

Lambda exonuclease digests the primers in a 5'>3' direction and terminates at the protecting group which his blocked by the presence of 1, 2, 3, or 4 consecutive phosphorothioate bonds, leaving a 3' ssDNA overhang on the opposite strand.

In some embodiments, the lambda exonuclease is used between 0.1 and 5 units. In other embodiments, the exonuclease reaction is used with 5-20 units.

The 3' overhang is subsequently blunted with an ssDNA specific 3'>5' exonuclease, such as Exonuclease I and/or Exonuclease T, Klenow Large Fragment of Pol I (exo+), and/or T4 DNA polymerase. To minimize gap filling by T4 DNA polymerase, the buffer system is designed with low dNTPs and high dATP concentrations.

In various embodiments, T4 DNA polymerase blunts the 3' overhang when combined with T4 PNK in the presence of 1 mM dATP.

In some embodiments, the T4 PNK is used between 1 and 10 units, and in other embodiments T4 PNK is used from 10-20 units per reaction.

In some embodiments, the T4 DNA polymerase is used between 0.1 and 0.5 units. In other embodiments the T4 DNA polymerase is used with 0.5 and 20 units per reaction.

In some embodiments, unexpectedly, blunt end products are more effectively generated when Exonuclease I and/or Exonuclease T are combined with Pfu (Exo +) and/or Klenow (Exo+) Large Fragment.

The dsDNA specific 5'>3' exonuclease and ssDNA specific 3'>5' exonuclease are compatible enzymes that can be combined with a kinase as a pre-mixture allowing multiple enzyme digestions in a single step thereby speeding up the overall workflow.

In some embodiments, a relatively high pH (>8.5) buffer is used with Pfu DNA polymerase buffer which is compatible with the pH of the selected exonuclease enzyme digest pre-mix so the buffer conditions do not need to be adjusted before partial primer digestion, thus saving additional steps, reagents and time.

In various embodiments, the primer digestion step is carried out in a standard PCR plate and incubated on a thermal cycler. The incubation temperatures can range from 0° C. to 37° C. In some embodiments, 20° C. is the preferred temperature when T4 DNA polymerase is used in combination with Lambda exonuclease and T4 PNK. The time of the incubation steps can vary from 1 to 60 minutes. However, different enzyme systems employ different times and temperature settings.

Any suitable dsDNA specific 5'>3' exonucleases can be used. In various embodiments, Lambda exonuclease is preferred, although T7 exonuclease can also be substituted.

According to various embodiments, there are many 3'>5' ssDNA specific exonucleases or polymerases that can be used to complete the DNA blunting or polishing of the 3' overhang product, including, but not limited to: Exonuclease I, Exonuclease T, T5 Exonuclease, RecJf, Exonuclease V (RecBCD), Nuclease BAL-31, Mung Bean Nuclease, Exo III, Klenow Large Fragment (Exo +), Pfu DNA polymerase, T4 DNA Polymerase, Bst, and Phi29.

Figure 2:
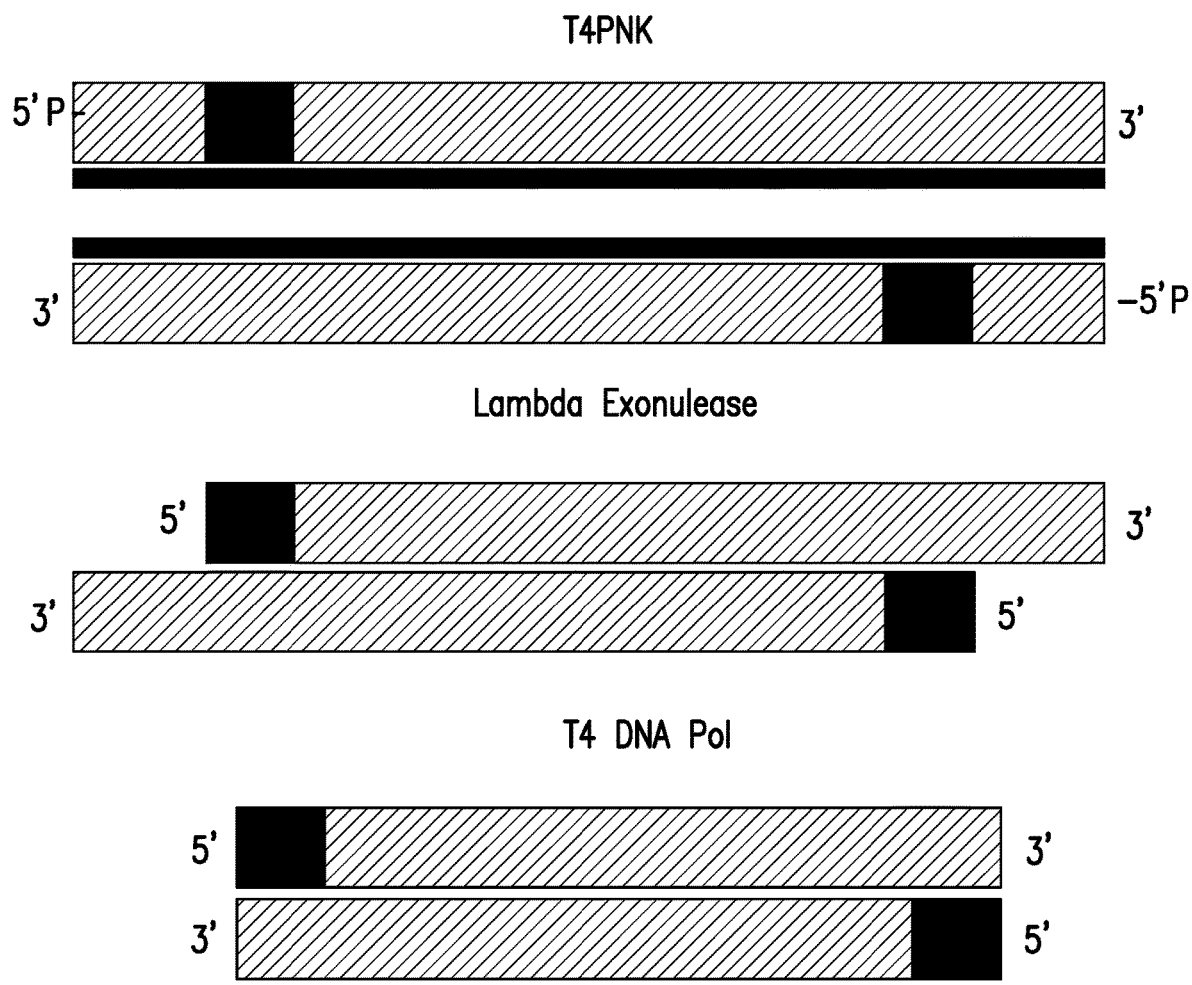
FIG. 2 shows how the T4 polynucleotide kinase prepares the 5' end of the amplicon by adding a 5' phosphate to the amplicon. The kinase allows the double-strand specific 5'>3" lambda exonuclease to digest the single stand until it terminates at the phosphorothioate protecting group. The T4 DNA polymerase then completes the digestion of the 3' overhand by shifting the reaction toward exonuclease rather than polymerase activity creating a blunt end.

With reference now to FIG. 2, the T4 polynucleotide kinase prepares the 5' end of the amplicon by adding a 5' phosphate to the amplicon. The kinase allows the double-strand specific 5'>3" lambda exonuclease to digest the single strand until it terminates at the phosphorothioate protecting group. The T4 DNA polymerase then completes the digestion of the 3' overhand by shifting the reaction toward exonuclease rather than polymerase activity creating a blunt end.

Heat Inactivation of Enzymes:

Many of the enzymes contemplated for use herein can be heat-inactivated except Pfu polymerase, which is highly thermostable at >95° C. Pfu DNA polymerase can be purified away via AMPURE XP® reagent using the SPRI method or blocked via the addition of additional Hot Start specific antibodies to the reaction.

Exemplary enzymatic primer digestion thermal cycler parameters and reaction conditions are as follows.

| Stage | Step | Temperature | Time |
|---|---|---|---|
| Hold | Exonuclease digestion | 0-20° C. | 1-60 min. |
| Hold | Heat inactivation of Enzymes | 60-85° C. | 1-30 min. |
| Hold | Stop | 10° C. | Infinity | dA-Tailing:

Some sequencing library preparation workflows require a T/A based adaptor ligation (e.g. Illumina sequencing platform), the digested product can be combined with a Taq Polymerase to modify the ends of the product via the preferential addition of a 3' adenosine (A-tailing) and then processed through the size selection and purification. In some embodiments, Klenow (exo-) can also be used to perform dA tailing in the presence of excess dATP. In other embodiments, Taq polymerase is used for dA tailing.

Purification:

In various embodiments, large fragment size selection and library purification of the digested amplified product is performed using the SPRI method (i.e. Agencourt AMPURE XP® reagent). Using a low concentration of bead reagent to original sample volume ratio (0.5×-0.8×), one can remove large amplification by-products and other large genomic DNA contaminants or high molecular weight DNA. The supernatant is retained and a subsequent SPRI step is performed to capture the target library. This is done by using a relatively high concentration of bead-to-supernatant-sample volume of (1.4×-1.8×).

Large concatemers can further be washed away via size selection using the SPRI method (solid-phase reversible immobilization).

Adaptor Ligation:

The known standard next-generation sequencing platforms require the ligation of adaptors to the amplicons for subsequent downstream NGS sequencing. However, any DNA ligase or even chemical ligation such as click-chemistry can be employed.

In various embodiments, ligation of sequencing platform-specific (e.g. Ion Torrent or Illumina) adaptor oligos are used which contain universal primer sequences (for subsequent library amplification) and barcode sequences (for processing multiple samples in a single sequencing run for downstream amplification) are used. The present teachings envision the use of adaptors that contain unique molecular index (UMI's) sequences.

In various embodiments, sequencing adapters are joined to both ends of the targeted insert regions using a ligase. The ligase can be, for example, one or more of the following: T4 DNA ligase, 9NTM DNA ligase, Taq DNA ligase, Tth DNA ligase, Tfi DNA ligase, Ampligase R, etc.

DNA Library Purification:

The DNA library purification step removes enzymes and incompatible buffers after the adaptor ligation and post-adaptor ligation digestion step. The SPRI method can be used for DNA library purification. In this step, the beads are used to select the appropriate fragments and remove contaminating excess adaptors. Relative to the first size purification step, this employs a significantly higher concentration (1.0×-2.2× bead-to-sample-volume ratio) of AMPURE XP® reagent so that adaptor-ligated amplicons (total size of 200-300 bp) are retained on the beads, while nucleotides, dNTP's, ligase, unligated adaptor oligos, and other contaminants can be washed away. The bead is saved and the targeted amplicons are then eluted from the beads using a low ionic strength solution such as nuclease-free water.

In various embodiments, the PCR library is quantified using quantitative real-time qPCR, Agilent's BioAnalyzer® DNA 1000 chip, or Qubit® DS DNA assay 4.0 fluorometer. In this step, equal amounts of different libraries can be pooled and amplified using universal primers.

In various embodiments, the prepared libraries are sequenced on the Life Technologies Proton using PI chips and/or the Illumina MiSeq.

In various embodiments, the present teachings are employed for targeted DNA re-sequencing applications. However, other embodiments contemplate, for example, RNASeq or whole exon or whole genome sequencing (via the use of random hexamers that contain protecting groups on the 3' end of the primer). Methods according to various embodiments of the present teachings can be used, for example, to detect gene variants such as insertions, deletions or single nucleotide polymorphisms (SNPs), to detect coding and/or non-coding somatic or germline mutations present in a sample that may be linked to increasing risk of a disease (prognosis) or for example, to diagnose a mutation in a solid tumor cancer sample.

In accordance with various embodiments, the present teachings can also be used, for example, for other next-generation sequencing methodologies, including DNAseq, RNAseq, MethylSeq, and ChIPseq which can be done by using a different source of the input material. In the case of RNAseq, for example, a first-strand cDNA synthesis can be produced using exonuclease protected primers. Also, the primer design program considers the mRNA sequence instead of the genomic sequence.

Kits:

Another aspect of the present teachings encompasses kits for preparing a plurality of amplification products with reduced non-specific amplification artifacts. For example, according to various embodiments, such a kit can comprise: (a) two or more pairs of non-5'phosphorylated amplification primers, each amplification primer comprising no more than four protecting groups (e.g., phosphorothioate bonds) in its 3' region; (b) a DNA polymerase; (c) a 5' to 3' exonuclease; (d) either a 3' to 5' single strand-specific exonuclease or a proofreading polymerase; (e) a 5' phosphorylating kinase; and, (f) one or more deoxynucleoside triphosphates (dNTPs).

In various embodiments, such a kit can further comprise one or more adaptors and/or a ligase, as described herein. Such a kit can additionally comprise one or more suitable buffers for each enzyme or combination thereof.

The kits provided herein generally include instructions for carrying out the processes described above. Instructions included in the kits can be affixed, for example, to packaging material or may be included as a package insert. While the instructions are typically written or printed materials, they are not limited to such. Any medium capable of storing such instructions and communicating them to an end user is contemplated by this disclosure. Such media include, but are not limited to, electronic storage media (e.g., magnetic discs, tapes, cartridges, chips), optical media (e.g., CD ROM), and the like. As used herein, the term "instructions" can include the address of an internet site that provides the instructions.

EXAMPLES

The following examples are illustrative and not intended to limit the scope of the present disclosure or appended claims.

Example 1

It has been reported that a 5' phosphorylated PCR primer is preferentially digested by lambda exonuclease over a non-phosphorylated PCR primer. (See, Nikiforov TT, Rendle RB, Kotewicz ML, Rogers YH. (1994) The Use of Phosphorothioate Primers and Exonuclease Hydrolysis for the Preparation of Single-stranded PCR Products and their Detection in Solid-phase Hybridization. PCR Methods Appl. 1994 Apr.; 3(5):285-91; incorporated herein by reference.)

When PCR primers are synthesized, they are typically made without a 5' phosphate unless a specific application requires it. Adding a 5' phosphate also adds costs which can quickly become significant when developing high-multiplex PCR panels. Therefore, it can be preferred to avoid the use of primers that are synthesized to include a 5' phosphate.

To overcome the use of synthesized PCR primers with a 5' phosphate, polynucleotide kinase (PNK) is added to Lambda exonuclease in the digestion enzyme system of (lambda exo/T4 PNK/dATP/T4 DNA polymerase). This digestion system comprises a relatively higher concentration of dATP in the digestion mix.

The unexpected observation in this digestion system is that the PCR primers are digested much faster (2×10×). Without committing to any particular theory, a rationale for this unexpected result is that PNK phosphorylated the 5' ends of the PCR primers, which in turn facilitated the attack by lambda exonuclease to digest the 5' end the PCR primer.

Further, experiments are performed at a lower temperature (20° C.), which is a temperature that is suboptimal for the activity of Lambda Exonuclease (37° C.). These digestion reactions are completed in 5 to 30 minutes and results are high reproducibility and consistent.

In this system, running the digestion reaction between 4° C. and 20° C. also provides a better double stranded template for the T4 DNA polymerase to attack and enable a 5'>3' exonuclease activity resulting in a blunt-end product.

Supplying the digestion reaction with a relatively high concentration of dATP helps drive T4 DNA polymerase towards an exonuclease function rather a DNA polymerase function.

Therefore, dATP provides a synergistic effect for both lambda exonuclease and T4 DNA polymerase in the digestion mixture.

PNK, in addition, phosphorylates the single stranded PCR primers that are not amplified. An advantage of using lambda exonuclease is that if the single stranded primer is 5' phosphorylated, lambda exonuclease will attack the unused primers and will digest until they reach the phosphorothioates. The 1-4 bases remaining are easily removed during bead clean up with AMPpure XP beads.

Further in these regards, see the table immediately below pertaining to various aspects of the digestion mix:

| Digestion Mix | | | |
|---|---|---|---|
| Component/Condition | Primary function | Secondary function | |
| Non-5'phosphorylated primers | PCR primers for target enrichment. | | |
| Lambda Exonuclease. | 5' > 3' exonuclease. Prefers double stranded template. | Highly preferential for 5' phosphate. | Optimal activity is 37° C. High temperature allows exonuclease attack at 5' end of oligo. |
| T4 DNA polymerase. PNK. | 3' > 5' exonuclease. 5' phosphorylation of PCR primer. | Generates blunt end products. Enables Lambda exonuclease to attack a double stranded PCR product at very low temperature. | Enables Lambda exonuclease to attack single-stranded primers and digest them. |
| High dATP/dNTP ratio. | Supplements Lambda exonuclease with phosphate groups for phosphorylation. | Drives T4 DNA polymerase towards 3' > 5' exonuclease. | |
| Low reaction temperature (4-20° C). | Keeps double stranded PCR product hybridized. | Enables T4 DNA polymerase to more effectively attack double stranded template for 3' > 5' exonuclease activity. | |

Example 2

This example describes how to prepare up to 96 barcoded Non-Small Cell Lung Cancer (NSCLC) next-generation sequencing (NGS) DNA libraries from formalin-fixed paraffin embedded (FFPE) samples directly from 5-15 um thick tissue sections or a cytology smear on a glass slide. This rapid, addition-only, 3.5 hour workflow is useful for the analysis of hundreds of actionable NSCLC mutations covering eight oncogenes (EGFR, KRAS, BRAF, NRAS, PIK3CA, PDGFRA, KIT and ALK) without the need for separate, labor intensive, and time-consuming, pre-analytical FFPE DNA extraction, purification, and isolation steps. The NSCLC two-pool design is comprised of only 26 primer-pairs per primer pool, thus allowing for ultra-sensitive mutation detection. The primer modification, as described herein, and unique primer-pair tiling design of the NSCLC panel enables high detection sensitivity and high-target specificity.

Target amplification by-products, which can significantly impede downstream NGS sequencing efficiency due to increased background noise, are substantially removed by way of the present workflow. This workflow can save significant time and enable higher target enrichment, leading to more sensitive detection of mutations from FFPE research samples. Typically, lower sequencing depth is required when using this workflow compared to standard multiplex PCR enrichment workflows, allowing for more sample barcoding per sequencing run.

The following reagent kits are employed:
SenseCare TargetPlex™ DNA Library Kit (Ion Torrent/ThermoFisher Compatible); and,
SenseCare TargetPlex™ NSCLC Panel, composed of Primer Pool 1 (PP1) and Primer Pool 2 (PP2).

Reagents provided in these kits are used to amplify targeted genomic regions directly from FFPE and add adapter barcode sequences to the amplicons.

The following reagent kit is recommended:
SenseCare Real-Time qPCR Library Quantification Kit (TaqMan) or SYBR® Green Real-Time PCR Kits.

Reagents provided in this kit allows for accurate DNA library quantification downstream of library preparation.

Input Recommendations:
Recommended input is ¼ to ½ tissue section on a slide per library preparation.
Recommended input is 1 cytology smear slide per library preparation.

Preparation of Highly Degraded FFPE Samples:
Highly degraded FFPE can still provide high-yield DNA libraries although the protocol may need to be adjusted with additional PCR amplification cycles.

STEP A: FFPE-Direct PCR Target Enrichment
This step uses PCR to amplify target regions of the DNA from FFPE tissue directly.

Reagents and Consumables Employed for Step A:
2× Ultra HiFi PCR Master Mix
5× NSCLC Primer Pool 1
5× NSCLC Primer Pool 2
100 µl or 200 µl pipette tip and a razor blade or Rainin wide-orifice pipette tips (Rainin Item number 30389248)
FFPE tissue (5-15 microns thick section on a standard glass slide or cytology smear)
Nuclease-free water
1.5 ml Eppendorf (or equivalent) tube
96-well PCR plate compatible with thermal cycler to be used
MicroAmp Clear Adhesive Film Set Up FFPE-Direct for PCR amplification:
1. Prepare PCR Mix by adding the following components into a 1.5 mL Eppendorf tube and mix well.

| COMPONENT | VOLUME PER SAMPLE |
| --- | --- |
| 2X Ultra Hi Fi PCR Master Mix | 30 µl |
| Nuclease-free water | 18 µl |
| Total per sample = | 48 µl |

2. Use a 100 µl or 200 µl pipette attached with a wide-orifice tip. If this is not available a tip can be prepared by cutting a standard 2001 tip approximately 3-5 mm up from the tip-end using sharp scissors or razor blade. The orifice diameter should be at least 3 mm. (Alternatively, purchase Rainin pipette tip item number 30389248).

3. Pipette all the 48 µl of the PCR mix onto at least half of the interested area of the FFPE tissue area on the slide.
4. Using a circular motion of the pipette tip, scrape the FFPE tissue off of the slide so that small bits of the FFPE can be seen suspended into the PCR mix.
5. Transfer 16 uL of the PCR Mix containing the FFPE bits into one clean PCR well.
6. Transfer a second 16 uL of the PCR Mix containing the FFPE bits into a second clean PCR well.
7. Add 4 µl of 5× NSCLC Primer Pool 1 (PP1) into the first PCR wells.
8. Add 4 µl of 5× NSCLC Primer Pool 2 (PP2) into the second PCR well. (Note: A 96-well PCR plate may be used if multiple FFPE samples are tested.)
9. Close the PCR tube or seal the 96-well PCR plate with a MicroAmp Clear Adhesive Film and briefly centrifuge.
10. Proceed to thermal cycling by running the following program steps as described below.

| STAGE | STEP | TEMP | TIME |
| --- | --- | --- | --- |
| Enz. Activation | Denature | 95° C. | 10 min. |
| Cycle | Denature | 99° C. | 15 sec. |
| (30-35 cycles)* | Extension | 60° C. | 4 min. |
| Hold | Stop | 10° C. | Infinity |

(Note:
Use more PCR cycles (i.e. up to 35 cycles) for highly degraded FFPE samples. Do not leave samples on Hold in the thermal cycler for more than 4 hours.)

11. After PCR thermal cycling is complete, briefly centrifuge the PCR products to bring the condensate to the bottom of the well.

STEP B: Enzymatic Primer Digestion
Reagents Employed for Step B:
10× Digestion Buffer
Digestion Enzyme Mix
Nuclease-free water
PCR tube (Optional) Ensure that the amplified PCR product yield is greater than 120 ng DNA by assessing with an Agilent Bio-analyzer or Qubit 4.0. (Note: less than 120 ng yield may not be sufficient for primer digestion and may require repeating Step A.)

Steps:
1. Combine Primer Pool 1 (PP1) with Primer Pool 2 (PP2) PCR products by pipetting PP2 products into PP1's PCR well. Note that either well would suffice.
2. Transfer only 20 µl of the combined PCR products into a new PCR tube or new 96-well Plate for enzymatic digestion.
3. Combine all the following components into the PCR tube and mix thoroughly.

| COMPONENT | VOLUME/SAMPLE |
| --- | --- |
| PP1 and PP2 Combined PCR Products | 20 µl |
| 20 µl 10X Digestion Buffer | 4 µl |
| Digestion Enzyme Mix | 2 µl |
| H2O | 14 µl |
| Total = | 40.0 µl |

5. Close the PCR tube or seal the 96-well PCR plate with MicroAMP clear adhesive film.
6. Incubate the reaction on a thermal cycler to allow primer digestion.

7. Place the tube in a thermal cycler and run the following program.

| STAGE | TEMP | TIME |
|---|---|---|
| Hold | 20° C. | 30 min. |
| Hold | 70° C. | 10 min. |
| Hold | 10° C. | Infinity |

8. Resuspend AMPure XP beads by inverting the bottle multiple times.
9. Add 72 μl (1.8×) of resuspended AMPure XP beads and mix well by pipetting up and down at least 10 times.
10. Incubate for 5 minutes at room temperature.
11. Place the tube on an appropriate magnetic stand to separate the beads from the supernatant. After the solution is clear (3 minutes), carefully discard the supernatant with a pipette. (Caution: Do not discard the BEADS as they contain the DNA library.)
12. Add 125 μl of freshly prepared 70% ethanol to the tube while in the magnetic stand. Incubate at room temperature for 30 seconds, and then carefully remove and discard the supernatant. Note: freshly prepared 70% ethanol solution is required to ensure best wash.
13. Repeat Step (12) one additional time.
14. Completely remove the residual ethanol and allow the beads to air dry for 5-7 minutes while the tube is on the magnetic stand with the lid open. Do not allow the beads to completely dry as the beads may flake off.
15. Elute the DNA target from the beads with 12 μl of nuclease-free water. Mix well by pipetting up and down and put the tube on the magnetic stand until the solution is clear.
16. Transfer the supernatant to a clean PCR tube (i.e., the eluted DNA library).

Immediately proceed to Step C to End-Repair (optional) or if end-repair is skipped, proceed immediately to Step E to Adaptor Ligation.

STEP C: End-Repair
(NOTE: THIS IS AN OPTIONAL STEP—USE ONLY FOR HIGHLY DEGRADED FFPE SAMPLES).

The end-repair step is optional and is intended for highly degraded FFPE samples. If this step is skipped proceed to Adaptor Ligation Step E.

Reagents Employed for Step C:
5× End-Repair Buffer
End-Repair Enzyme Mix
Nuclease-free water
PCR tube
Steps:
1. Combine the following end-repair components:

| COMPONENT | VOLUME/SAMPLE |
|---|---|
| Digested PCR Product (Step B) | 10 μl |
| 5x End-Repair Buffer | 4 μl |
| End-Repair Enzyme Mix | 0.2 μl |
| H2O | 5.8 μl |
| Total = | 20 μl |

2. Pipet up and down to thoroughly mix.
3. Incubate at room temperature for 20 minutes.
4. Immediately proceed to Step D: Purify End-Repair Product.

STEP D: Purify End-Repair Product
Using Beckman Coulter Agencourt AMPure XP magnetic beads at a low concentration to remove large genomic DNA.
Reagents and Equipment Employed for Step D:
Beckman Coulter Agencourt AMPure XP beads
Magnetic stand
Freshly prepared 70% ethanol solution
Nuclease-free water
Steps:
1. Resuspend AMPure XP beads by inverting the bottle multiple times.
(a) Add 36 μl (1.8×) of resuspended AMPure XP beads to 20 μl from Step C and mix well by pipetting up and down at least 10 times.
(b) Incubate for 5 minutes at room temperature.
(c) Place the tube on an appropriate magnetic stand to separate the beads from the supernatant. After the solution is clear (3 minutes), carefully discard the supernatant with a pipette. Caution: Do not discard the beads as they contain the DNA library.
(d) Add 125 μl of freshly prepared 70% ethanol to the tube while in the magnetic stand. Incubate at room temperature for 30 seconds, and then carefully remove and discard the supernatant. Note: freshly prepared 70% ethanol solution is recommended to ensure best wash.
(e) Repeat Step (d) one additional time.
(f) Completely remove the residual ethanol and allow the beads to air dry for 5-7 minutes while the tube is on the magnetic stand with the lid open. Do not allow the beads to completely dry as the beads may flake off.
(g) Elute the DNA target from the beads with 12 μl of nuclease-free water. Mix well by pipetting up and down and put the tube on the magnetic stand until the solution is clear.
(h) Transfer the supernatant to a clean PCR tube (i.e., contains the eluted DNA library).

STEP E: Adaptor Ligation
This step allows the ligation of the sequencing adaptors to the DNA library.
Reagents Employed for Step E:
10× Ligation Buffer
Ligation Enzyme Mix
Ion Adaptor Barcode PCR Tube—comes as an 8-well strip
Nuclease-free water In a PCR tube, combine the reagents as indicated in the table below. (Note: Add the components in the order listed.)
1. Centrifuge the Ion Adaptor Barcode 8-well PCR tubes which contain 1 μl tube of the Ion Adapter Barcodes per tube.
2. Carefully open the caps of one Ion Adaptor Barcode PCR Tube.
3. Transfer 10 μl of the Enzymatic Primer Digested Product (Step B) or Purified End-Repaired Product (Step D) to one Ion Adapter Barcode Tube.
4. Mix by pipetting up and down several times well.
5. Record the Barcode ID used with your sample.
6. Add the remaining components (10× Ligation Buffer, Ligation Enzyme Mix, nuclease-free water) as shown in the table below. Mix well.

Ion Torrent Adaptor Ligation Reaction Set-Up:

| COMPONENT | VOLUME/SAMPLE |
|---|---|
| Ion Torrent Adaptors | 1.0 μl (step 1) |
| Product from Step B or Step D | 10.0 μl (step 3) |

-continued

| COMPONENT | VOLUME/SAMPLE |
| --- | --- |
| 10X Ligase Buffer | 2.0 µl (step 6) |
| Ligase Enzyme Mix | 2.0 µl (step 6) |
| H2O | 5.0 µl (step 6) |
| Total = | 20.0 µl |

7. Cover the tube and centrifuge the contents.
8. Place the tube in a thermal cycler and run the following programmed steps.

| STAGE | STEP | TEMP | TIME |
| --- | --- | --- | --- |
| Hold | Ligation | 25° C. | 30 min. |
| Hold | Enzyme Denature | 72° C. | 5 min. |
| Hold | Stop | 4° C. | infinity |

9. Immediately proceed to Step F: Amplify DNA Library once the reaction reaches the 4° C. Stop step.
STEP F: Amplify DNA Library
This step removes residual library adaptors, ligation buffers and prepares the DNA library for final PCR amplification.
Reagents and Equipment Employed for Step F:
Beckman Coulter Agencourt AMPure XP beads
Magnetic stand
Freshly prepared 70% ethanol solution
2× SenseCare HiFi PCR Master Mix
10× Ion Library Amplification Primer Mix
Nuclease-free water
Steps:
1. Resuspend AMPure XP beads by inverting the bottle multiple times.
2. Add 20 µl (1.0×) of resuspended AMPure XP beads to 20 µl of the adaptor ligated PCR library from Step D. Mix well and incubate for five (5) minutes at room temperature.
3. Place the tube on an appropriate magnetic stand to separate the beads from the solution. After the solution is clear (at least 3 minutes). (Caution: Do not discard the BEADS as they contain the DNA library of interest.) Carefully remove the supernatant and discard.
4. Add 125 µl of freshly prepared 70% ethanol to the tube while on the magnetic stand. Incubate at room temperature for 30 seconds, and then carefully remove and discard the supernatant.
5. Repeat wash step (Step 4).
6. Completely remove the residual ethanol, and air-dry beads for 5 minutes while the tube is on the magnetic stand with the tube's lid open.
7. To each well containing a magnetic beads, add 50 µl of the following mixture of components:

| COMPONENT | VOLUME/SAMPLE |
| --- | --- |
| 2x SenseCare HiFi PCR Master Mix | 25 µl |
| 10X Ion Library Amp Primer Mix | 5 µl |
| Nuclease-free water | 20 µl |
| Total = | 50 µl |

8. Run on a thermal cycler with the following programmed steps.

| STAGE | STEP | TEMP | TIME |
| --- | --- | --- | --- |
| Hold | Activation/Denaturation | 98° C. | 2 min. |
| Cycle | Denaturation | 98° C. | 15 sec. |
| (×10–14)* | Annealing/Extension | 64° C. | 1 min. |
| Hold | Stop | 10° C. | infinity |

(Note:
Use more PCR cycles (i.e. up to 14 cycles) for highly degraded FFPE samples.)

(Note: Use more PCR cycles (i.e. up to 14 cycles) for highly degraded FFPE samples.)
STEP G: Purify Final DNA Library
Use AMPure XP magnetic beads to purify sequencing-ready DNA amplicon libraries.
Reagents and Equipment Employed for Step G:
Beckman Coulter Agencourt AMPure XP beads
Magnetic stand
Eppendorf LoBind PCR tubes or plates
Freshly prepared 70% ethanol solution
Nuclease-free water or Low TE buffer
MicroAmp Clear Adhesive Film
Steps:
1. Resuspend AMPure XP beads by inverting bottle multiple times.
2. Add 25 µl (0.5×) of resuspended AMPure XP beads to the 50 µl of library and mix well by pipetting up and down at least 10 times.
3. Incubate for 5 minutes at room temperature.
4. Place the tube on the magnetic stand to separate the magnetic beads from the supernatant.
5. After the solution is clear (3 minutes), carefully pipette the supernatant approximately 75 µl containing the desired amplicon library to a new well. Small amounts of bead carryover do not affect performance.
6. Add 60 µl AMPure XP beads (0.8×) to each well containing the transferred supernatant 75 µl.
7. Pipette up and down to briefly mix solutions.
8. Incubate at room temperature for 5 minutes.
9. Place on the magnetic stand and wait until the liquid is clear (3 minutes).
10. Without disturbing the beads, remove and discard the supernatant. Note: The amplicon library is captured on the beads.
11. Add 1250 of freshly prepared 70% ethanol to the tube while on the magnetic stand. Incubate at room temperature for 30 seconds, then without disturbing the bead pellet, carefully remove, and discard the supernatant. Note: freshly prepared ethanol solution is recommended to ensure best performance.
12. Repeat previous 70% ethanol wash (Step 11).
13. Use a 20 µl pipette to remove and discard all residual EtOH from each well. Note: This is a important step.
14. Air dry the magnetic beads for 5 minutes while the tube is on the magnetic stand with lid open. Do not allow the beads to completely dry as the beads may flake off.
15. Elute the DNA library from the beads with 20 µl of nuclease-free water or Low TE buffer. Mix thoroughly by pipetting up and down.
16. Incubate at room temperature for 5 minutes.
17. Place on the magnetic stand and wait until the liquid is clear (3 minutes).
18. Transfer the supernatant (approximately 20 µl) containing the DNA library to a clean Eppendorf LoBind PCR plate or tube for storage.
19. Ensure the plate is well sealed and store at −25° C. to −15° C.

STEP H: Library Quantity and Quality Assurance—For Ion Torrent DNA Libraries

Perform the following procedures for quality control analysis.

Reagents and Equipment Employed for Step H:
2100 BioAnalyzer Instrument with Bioanalyzer DNA 1000 Chip Kit (Agilent Technologies, Inc.)
qPCR Library Quantification Kit for Ion Torrent (use either probe-based or SYBR® Green Real-Time PCR Kits) both available through SenseCare
Qubit 4.0 Fluorometer with the Qubit dsDNA BR Assay Kit (Life Technologies/ThermoFisher)

Bioanalyzer (Use for Accurate DNA Library Fragment Quality Control.)
1. Analyze 1 µl library using the Agilent 2100 Bioanalyzer with the Agilent DNA 1000 Kit.
2. See (1) Agilent Bioanalyzer 2100 User's Guide (Edition 02/02; p/n: G2941-90002; Agilent Technologies, Inc.) and (2) Agilent DNA 1000 Kit Guide (Edition 12/2016; p/n: G2938-90014 Rev. C; Agilent Technologies, Inc.) for details (each of which is incorporated herein by reference).

Final TargetPlex FFPE-Direct NSCLC Bar-Coded DNA Library for Ion Torrent NGS Sequencing.

Figure 3:
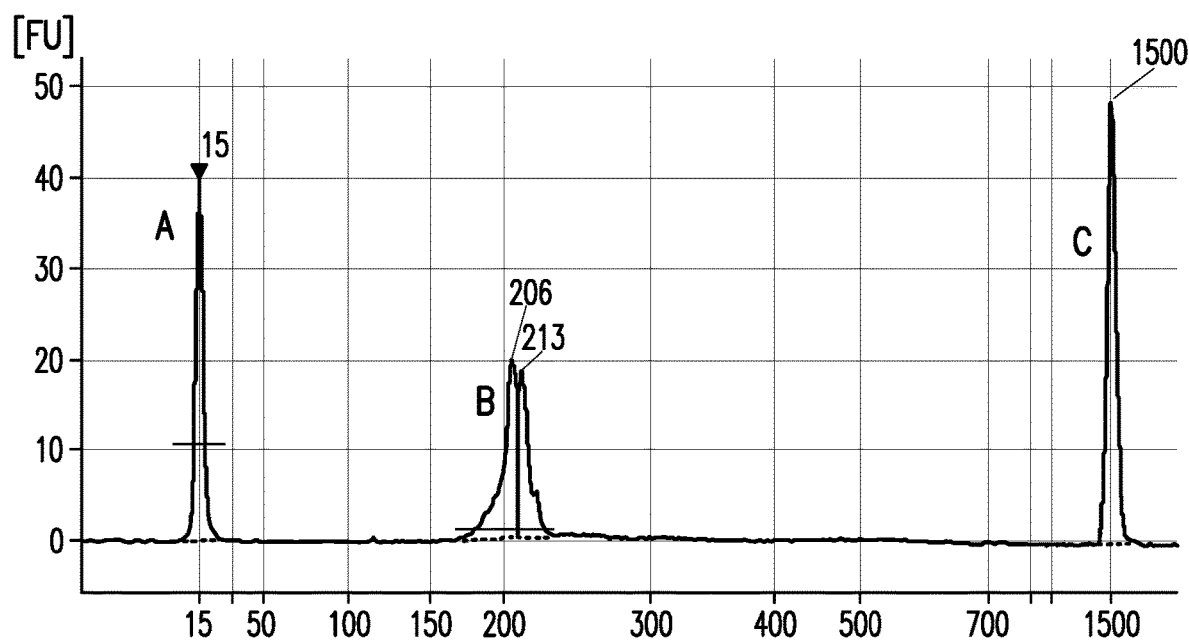
FIG. 3 shows the final Non-Small Cell Lung Cancer (NSCLC) Bar-coded DNA Library for Ion Torrent NGS Sequencing.

See FIG. 3: TargetPlex NSCLC FFPE—Library Bioanalyzer Profile Expected DNA library fragment profile distribution is between 150-220 bps on a DNA 1000 Chip. (A=Lower marker; B=Expected libraries; C=Upper marker.)

qPCR Library Quantification Kits (Use for accurate DNA Library quantification analysis.)
1. Quantify 1 µl library by qPCR using SenseCare TaqMan or SYBR® Green Real-Time PCR kits.

Qubit 4.0 (Use for accurate DNA library yield analysis.)
1. Analyze 1 µl library using the Qubit Fluorometer with the Qubit dsDNA BR Assay Kit
2. For fluorometric methods, calculate the molarity (nM) of the library using the following formula: ng/uL*1,000,000/660/210=nM Example 3

The following figures are illustrative of results for the foregoing protocol and their interpretation.

Figure 4A:
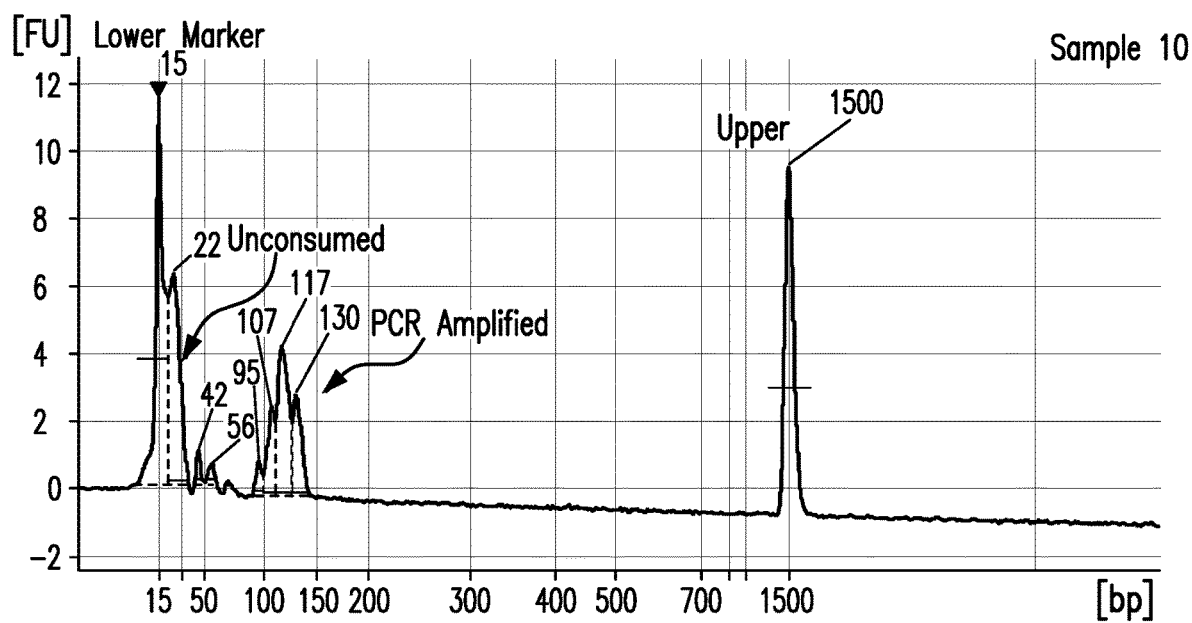
FIG. 4A shows a Bioanalyzer trace of the multiplex PCR amplified product before digestion.

FIG. 4A shows a Bioanalyzer trace of multiplex PCR amplified product before digestion.

Figure 4B:
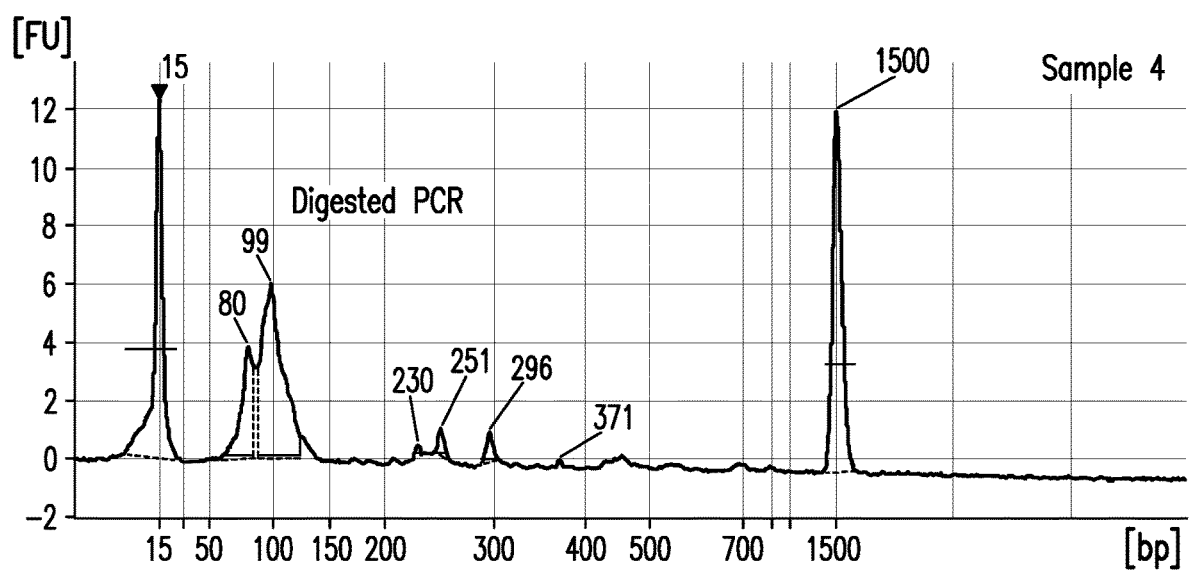
FIG. 4B shows a Bioanalyzer trace of the multiplex PCR amplified product after digestion. A shift in the DNA peak to the left demonstrates that the PCR primers were partially digested and excess unused PCR primers from the amplification step were removed.

FIG. 4B shows a Bioanalyzer trace of multiplex PCR amplified product after digestion. A shift in the DNA peak to the left demonstrates that the PCR primers are partially digested and excess unused PCR primers from the amplification step are removed.

Figure 5:
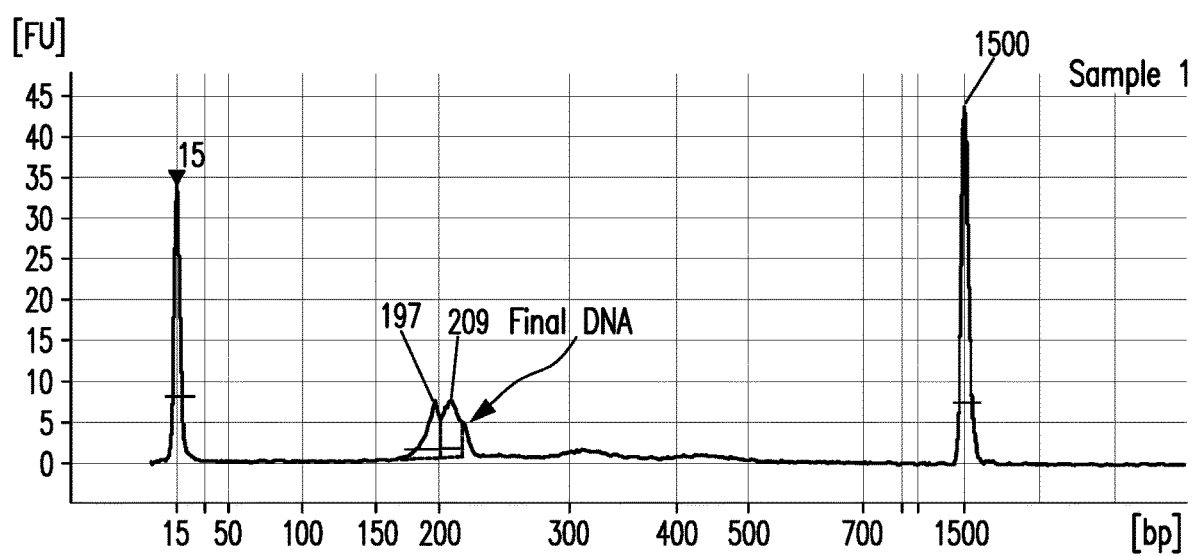
FIG. 5 shows a Bioanalyzer trace of the final DNA library after adaptor ligation; and, FIG. 6 shows an overlay of undigested and digested product.

FIG. 5 shows a Bioanalyzer trace of the final DNA library after adaptor ligation.

Figure 6:
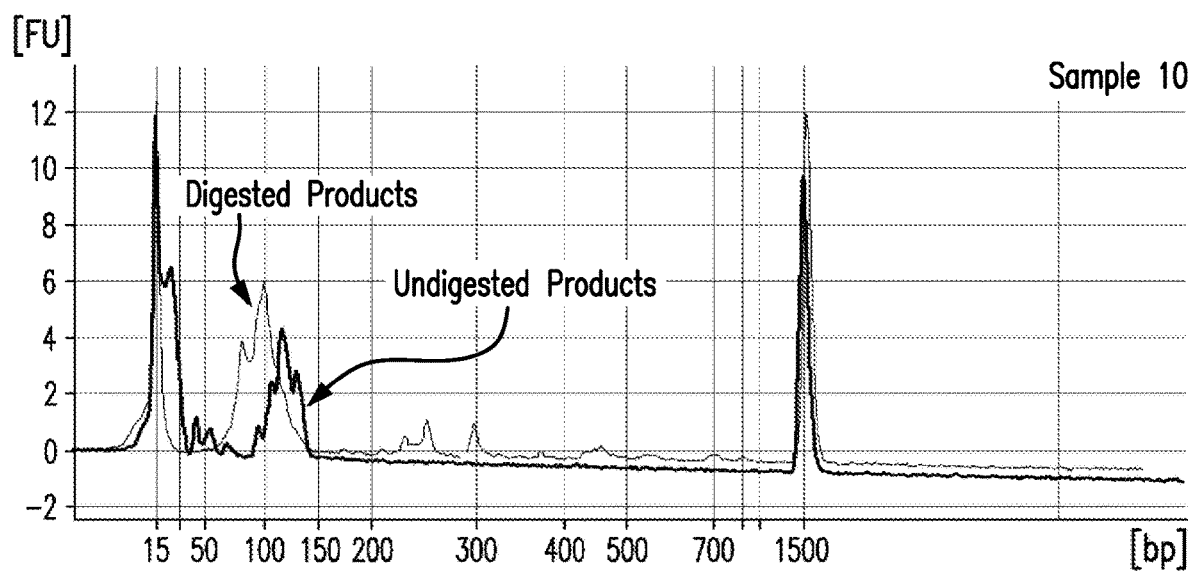

FIG. 6 shows an overlay of undigested and digested product.

All references set forth herein are expressly incorporated by reference in their entireties for all purposes.

Those skilled in the art can now appreciate from the foregoing description that the broad teachings herein can be implemented in a variety of forms. Therefore, while the present teachings have been described in connection with various embodiments and examples, the scope of the present teachings is not intended to, and should not be construed to be, limited thereby. Various changes and modifications can be made without departing from the scope of the present teachings.

The invention claimed is:

1. A process for preparing a plurality of multiplex amplified nucleic acid products for targeted next generation-sequencing providing reduced background noise, comprising:
    (a) contacting one or more nucleic acids with at least two pairs of non-5'phosphorylated amplification primers and a DNA polymerase under amplification conditions to form a plurality of amplification products, each amplification primer comprising at least one and no more than four protecting groups in its 3' region; and wherein the protecting groups are phosphorothioate bonds; and
    (b) contacting the plurality of amplification products with a mixture comprising (i) a 5' to 3' exonuclease, (ii) either a 3' to 5' single strand-specific exonuclease or a proofreading polymerase, and (iii) a 5' phosphorylating kinase, to form a plurality of digested and phosphorylated amplification products;
wherein the 5' to 3' exonuclease comprises lambda exonuclease; and
wherein step (b) is carried out at a reaction temperature of about 20° C. or less; and further
wherein the plurality of digested and phosphorylated amplification products has a reduced level of non-specific amplification artifacts as compared to a standard nucleic acid amplification reaction performed with primers devoid of protecting groups.

2. The process of claim 1, wherein the 5' phosphorylating kinase comprises T4 polynucleotide kinase (T4 PNK).

3. The process of claim 1, wherein the 3' to 5' exonuclease comprises T4 DNA polymerase.

4. The process of claim 1, wherein the DNA polymerase of step (a) lacks a proofreading activity.

5. The process of claim 1, wherein the DNA polymerase of step (a) comprises a proofreading activity.

6. The process of claim 1, wherein the amplification primers further comprise at least one terminal 5' base mismatch.

7. The process of claim 1, wherein step (b) further comprises contacting the plurality of amplification products with a plurality of dNTPs selected from the group consisting of dATP, dGTP, dCTP, and dTTP; wherein one of the dNTPs is present at a concentration that is higher compared to the concentration of the other dNTPs, whereby presence of the excess dNTP shifts the digestion reaction of step (b) towards an exonuclease function rather than a polymerization function.

8. The process of claim 1, further comprising ligating one or more adaptors to the plurality of digested amplification products to form a plurality of adaptor-ligated amplification products.

* * * * *